United States Patent [19]

Yazaki et al.

[11] Patent Number: 5,158,775
[45] Date of Patent: Oct. 27, 1992

[54] AEROSOLS OF PYRIDO [1,2-A]PYRIMIDINE COMPOUNDS

[75] Inventors: Takashi Yazaki, Misato; Yukio Goto, Tokyo, both of Japan

[73] Assignee: Tokyo Tanabe Company, Limited, Tokyo, Japan

[21] Appl. No.: 538,104

[22] Filed: Jun. 14, 1990

[30] Foreign Application Priority Data

Jun. 15, 1989 [JP] Japan .................................. 1-150540
Jun. 20, 1989 [JP] Japan .................................. 1-155798

[51] Int. Cl.$^5$ ................................. A61K 9/12
[52] U.S. Cl. ..................... 424/45; 514/662; 514/676; 514/678; 514/680; 514/687; 514/715; 514/716; 514/717; 514/718; 514/724; 424/46; 424/434
[58] Field of Search ............ 424/434, 45, 46; 514/662, 676, 678, 680, 687, 715, 716, 717, 718, 724

[56] References Cited

FOREIGN PATENT DOCUMENTS 0217673 4/1987 European Pat. Off. .
0242230 10/1987 European Pat. Off. .
246375 2/1987 Japan .
243082 3/1987 Japan .
246374 4/1987 Japan .

*Primary Examiner*—Thurman K. Page
*Assistant Examiner*—C. Azpuru
*Attorney, Agent, or Firm*—McGlew & Tuttle

[57] ABSTRACT

A suspension type aerosol inhalations containing (a) 0.015 to 5.00% (w/w) of a pyrido[1,2-a]pyrimidine compound of the formula:

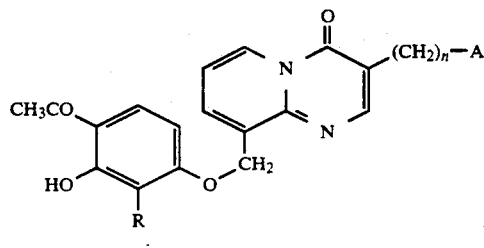

where R is a n-propyl or allyl group, A is a tetrazolyl or carboxyl group, and n is a whole number of 0 to 2, and (b) 0.015 to 5.00% (w/w) of a fatty acid ester.

11 Claims, No Drawings

AEROSOLS OF PYRIDO [1,2-A]PYRIMIDINE COMPOUNDS

BACKGROUND OF THE INVENTION

1. Field of the Invention

This invention relates to aerosols of antiallergic drugs and, more particularly, to suspension type aerosol inhalations containing pyrido[1,2-a]pyrimidine compounds of the formula:

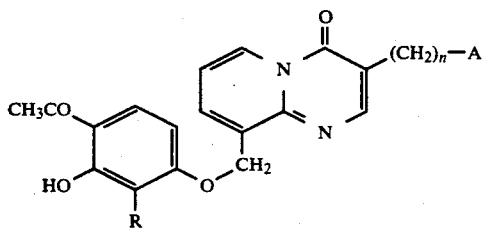

where R is a n-propyl or allyl group, A is a tetrazolyl or carboxyl group, and n is a whole number of 0 to 2.

2. Description of the Prior Art

Pyrido[1,2-a]pyrimidine compounds represented by the above formula are the compounds disclosed in Japanese Patent Laid-Open Nos. 242682/'87, 183581/'88 and 246375/'88. It is described therein that these compounds have a powerful inhibitory effect on leukotrien D4 known to be a representative active component of slow-reacting substance of anaphylaxis (hereinafter referred to as SRS-A) and, therefore, are useful as drugs for the treatment of Type I allergic diseases induced by SRS-A.

At present, commercially available antiallergic agents are principally in the form of oral preparations. However, oral preparations are not always regarded as a proper dosage form, because they generally involve an increase in dose and hence lead to the manifestation of side effects. Especially for bronchial asthma and allergic rhinitis, topical preparations for applying a drug directly to the affected part, particularly inhalations, are considered to be an effective dosage form in that they can produce drug effects efficiently and mitigate side effects.

Inhalations for use as antiallergic agents included aqueous solution type aerosol inhalations, solution type aerosol inhalations and suspension type aerosol inhalations. The solubilities of pyrido[1,2-a]pyrimidine compounds in water are very low. For example, the solubility of 9-[(4-acetyl-3-hydroxy-2-n-propylphenoxy)methyl]-3-(1H-tetrazol-5-yl)-4-H-pyrido[1,2-a]pyrimidin-4-one (hereinafter referred to as AS-35) in water is as low as 0.4 µg/ml. Accordingly, it would be impractical to prepare an aqueous solution type aerosol inhalation of AS-35, because this requires massive containers and devices. Moreover, in order to prepare a solution type aerosol inhalation of a pyrido[1,2-a]pyrimidine compound, it must be dissolved in a propellant or a mixture of a propellant and a commonly used solubilizing agent. However, AS-35 is entirely insoluble in commonly used propellants including trichloromonofluoromethane (Freon 11), dichlorodifluoromethane (Freon 12), monochlorotrifluoromethane (Freon 13), dichloromonofluoromethane (Freon 21), monochlorodifluoromethane (Freon 22), trichlorotrifluoroethane (Freon 113), dichlorotetrafluoroehtane (Freon 114), monochloropentafluoroethane (Freon 115), 2,2-dichloro-1,1,1-trifluoroethane (Freon 123), 2-chloro-1,1,1,2-tetrafluoroethane (Freon 124), 1,2-dichloro-2,2-difluoroethane (Freon 132b), 1 chloro-2,2,2-trifluoroethane (Freon 133a), 1,1,1,2-tetrafluoroethane (Freon 134a), 1,1-dichloro-1,1,1-trifluoroethane (Freon 141b), 1-chloro-1,1-difluoroethane (Freon 142b), 1,1-difluoroethane (Freon 152a), 3-3-dichloro-1,1,1,2,2-pehtafluoropropane (Freon 225ca), 1,3-dichloro-1,1,2,2,3-pentafluoropropane (Freon 225cb) and octafluorocyclobutane (Freon C318). Moreover, AS-35 is also insoluble in mixtures of such propellants and commonly used solubilizing agents. Thus, it is impossible to prepare a solution type aerosol inhalation of AS-35.

The present invention is concerned with inhalations containing pyrido[1,2-a]pyrimidine compounds that are antiallergic drugs, and is directed to the provision of suspension type aerosol inhalations which are easy to carry and handle.

The requirements for suspension type aerosol inhalations are that the drug is suspended in the propellant and the dispersant, that the amount delivered is kept constant, that the drug particles are fine, and that they are physicochemically stable during long-term storage.

Delivery of the suspension in constant amounts means that the drug is applied to the affected part in constant doses. To this end, it is essential that the dispersibility of drug particles in the propellant be good. Accordingly, it is necessary to use dispersant which dissolves in the propellant and prevents the cohesion of drug particles. Moreover, the drug must not be soluble in the propellant or the dispersant because the crystals in drug particles may grow during long-term storage to cause clogging of the valve or variation in the amount delivered.

In order to allow a pyrido[1,2-a]pyrimidine compound to reach the affected part effectively, it is important that the pyrido[1,2-a]pyrimidine compound be in the form of fine particles. More specifically, it is preferable that the particles diameters be in the range of 0.01 to 10 µm and at least 50% of the particles have a diameter of 2 to 5 µm. Pyrido[1,2-a]pyrimidine compounds having such minute particle diameters can be obtained by pulverizing coarse particles thereof.

However, fine particles of pyrido[1,2-a]pyrimidine compounds (hereinafter referred to briefly as fine particles) tend to cohere. In order to prepare suspension type aerosol inhalations, such fine particles must be dispersed in a propellant.

For example, it has been reported that, when suspension type aerosol inhalations were prepared by using a pyrido[1,2-a]pyrimidine compounds selected from AS-35 and [9-(4-acetyl-3-hydroxy-2-n-propylphenoxymethyl)-4-oxo-pyrido[1,2-a]-pyrimidin-3-yl]-acetic acid (hereinafter referred to as AS-148), a propellant comprising a 4:6 mixture of Freon 11 and Freon 12, and a commonly used dispersant selected from propyleneglycol didecanoate (hereinafter referred to as PDD), diglyceryl mono-oleate (hereinafter referred to as DGMO-C), glyceryl dioleate (hereinafter referred to as DGO-80), tetraglyceryl hexacaprylate (hereinafter referred to as Sefsol 668), hexamethyltetracosane (hereinafter referred to as squalane), isopropyl myristate (hereinafter referred to as IPM) and polyoxyethylene (20) sorbitan mono-oleate (hereinafter referred to as Tween 80), the fine particles of AS-35 or AS-148 cohered to cause clogging of the valve or variation in the amount delivered. The present inventors have confirmed these findings by their own experiments. On the basis of their similarity in physicochemical properties, other pyrido[1,2-a]pyrimidine compounds are expected to behave in the same manner as AS-35 and AS-148.

SUMMARY OF THE INVENTION

In view of the above-described existing circumstances, the present inventors made an intensive study of suspension type aerosol inhalations containing pyrido[1,2-a]pyrimidine compounds. As a result, it has been found that, if a suspension type aerosol inhalation containing a finely powdered pyrido[1,2-a]pyrimidine compound is prepared by using a sorbitan fatty acid ester or a decaglycerin fatty acid ester as a dispersant, the resulting aerosol inhalation shows little variation in the amount delivered and remains physicochemically stable during long-term storage. The present invention has been completed on the basis of this finding.

According to the present invention, there is provided an aerosol composition containing (a) 0.015 to 5.00% (w/w) of a pyrido[1,2-a]pyrimidine compound of the formula:

$$\text{(structure shown)}$$

where R is a n-propyl or allyl group, A is a tetrazolyl or carboxyl group, and n is a whole number of 0 to 2, and (b) 0.015 to 5.00% (w/w) of a fatty acid ester.

DETAILED DESCRIPTION OF THE PREFERRED EMBODIMENTS

In the suspension type aerosol inhalations of the present invention, the pyrido[1,2 a]pyrimidine compound represented by the above formula is preferably present in an amount of 0.015 to 5.00% (w/w), and the sorbitan fatty acid ester or decaglycerin fatty acid ester is preferably present in an amount of 0.015 to 5.0% (w/w). The propellant may be any fluorine-containing lower hydrocarbon, and specific examples thereof include Freon 11, Freon 12, Freon 13, Freon 21, Freon 22, Freon 113, Freon 114, Freon 115, Freon 123, Freon 124, Freon 132b, Freon 133a, Freon 134a, Freon 141b, Freon 142b, Freon 152a, Freon 225ca, Freon 225cb, Freon C318 and mixtures thereof.

Useful pyrido[1,2-a]pyrimidine compounds include, for example, AS-35, 9-[(4-acetyl-3-hydroxy-2-n-propylphenoxy)methyl]-3-[2-(1H-tetrazol-5-yl)ethyl]-4H-pyrido[1,2-a]pyrimidin-4-one (hereinafter referred to as AS-163), 9-[(4 acetyl-3-hydroxy-2-allylphenoxy)methyl]-3-(1H-tetrazol-5-yl)-4H-pyrido[1,2-a]pyrimidin-4-one (hereinafter referred to as AS-168) and AS-148.

Useful sorbitan fatty acid esters include, for example, sorbitan sesquioleate (hereinafter referred to as SO-15), sorbitan mono-oleate (hereinafter referred to as SO-10), sorbitan trioleate (hereinafter referred to as SO-30) and sorbitan monoisostearate (hereinafter referred to as SI-10R).

Useful decaglycerin fatty acid esters include, for example, decaglyceryl decaoleate (hereinafter referred to as Decaglyn 10-O), decaglyceryl decastearate (hereinafter referred to as Decaglyn 10-S), decaglyceryl heptaoleate (hereinafter referred to as Decaglyn 7-O), decaglyceryl pentaoleate (hereinafter referred to as Decaglyn 5-O), decaglceryl trioleate (hereinafter referred to as Decaglyn 3-O), decaglyceryl dioleate (hereinafter referred to as Decaglyn 2-O) and decaglyceryl diisostearate (hereinafter referred to as Decaglyn 2-IS).

If necessary, the aerosol inhalations of the present invention can additionally contain density modifiers such as finely powdered sodium sulfate, calcium chloride and sodium chloride, and solidification inhibitors such as cetylpyridinium chloride and myristyl-gamma-picolinium chloride.

First of all, a series of experiments were carried out to evaluate the effectiveness of conventional dispersants. More specifically, various ester forms of non-ionic surfactants not irritating the site of application were tested by using an aerosol composition consisting of finely powdered AS-35 and a propellant comprising a 4:6 mixture of Freon 11 and Freon 12. Thus, the solubility of the dispersants in the propellant, the dispersibility of fine particles, the cohesiveness of fine particles, and variation in the amount delivered were examined. The results thus obtained are shown in Tables 1 and 2.

Among the aforesaid test items, the solubility of a dispersant in the propellant was evaluated by placing 90 mg of the dispersant in a transparent container made of polyethylene terephthalate (hereinafter referred to as PET), attaching a valve thereto, injecting the propellant (i.e., a 4:6 mixture of Freon 11 and Freon 12) thereinto until the contents amounted to 12.0 g, shaking the container vigorously, and then observing the contents with the naked eye. The dispersibility and cohesiveness of fine particles were evaluated by placing 90 mg of finely powdered AS-35 and 90 mg of a dispersant in a transparent container made of PET, attaching a valve thereto, injecting a propellant (i.e., a 4:6 mixture of Freon 11 and Freon 12) thereinto until the contents amounted to 12.0 g, shaking the container vigorously, allowing it to stand, and then observing the contents with the naked eye. The results thus obtained are shown in Table 1.

TABLE 1

| Formulation No. | Dispersant | Solubility | Dispersibility | Cohesiveness |
|---|---|---|---|---|
| 1 | PDD | Soluble | Good | High |
| 2 | DGMO-C | Soluble | Good | Low |
| 3 | DGO-80 | Soluble | Good | Low |
| 4 | Sefsol 668 | Insoluble | Poor | High |
| 5 | Squalane | Soluble | Good | Low |
| 6 | IPM | Soluble | Good | Low |
| 7 | Tween 80 | Insoluble | Poor | High |

AS-148 gave exactly the same results as AS-35. Similar results were also obtained when a 6:4 mixture of Freon 114 and Freon 12 was used as the propellant.

Variation in the amount delivered was evaluated by delivering the suspension ten times and calculating the average amount delivered at one time, from the weight loss of the transparent container made of PET. The results thus obtained are shown in Table 2.

TABLE 2

| Number of times of delivery | Average amount delivered at one time (mg) Formulation No. | | | | |
|---|---|---|---|---|---|
| | 1 | 2 | 3 | 5 | 6 |
| 1-10 | 97 | 114 | 98 | 115 | 115 |
| 11-20 | 83 | 113 | 103 | 114 | 114 |
| 21-30 | 76 | 114 | 83 | 112 | 113 |
| 31-40 | 85 | 115 | 72 | 113 | 115 |
| 41-50 | 65 | 113 | — | 98 | 114 |
| 51-60 | — | 97 | — | 105 | 110 |
| 61-70 | — | 106 | — | 88 | 93 |
| 71-80 | — | 89 | — | 75 | 84 |
| 80-90 | — | 73 | — | 103 | 105 |
| 91-100 | — | 54 | — | 83 | 76 |

*With Formulations 4 and 7, the valve became clogged at the start of delivery and no suspension was delivered. With Formulations 1 and 3, the valve became clogged in the course of the test and the suspension was delivered no longer. With Formulations 2, 5 and 6, the amount delivered was not kept constant.

As described above, various conventional dispersants were tested by using them to disperse AS-35 or AS-148. In any case, it was impossible to prepare a useful suspension type aerosol inhalation, because the cohesion of fine particles caused clogging of the valve or variation in the amount delivered. Other pyrido[1,2-a]pyrimidine compounds are expected to behave in the same manner as AS-35 and AS-148.

Next, the storage stability of suspension type aerosol inhalations in accordance with the present invention was evaluated. More specifically, they were tested for the growth of crystals in the fine particles of AS-35 or AS-148, for the presence of decomposition products, and for variation in the amount delivered. The growth of crystals was tested by measuring particle diameters under the microscope according to the procedure described in U.S.P XXI under Isoproterenol Hydrochloride and Phenylephrine Tartrate Aerosols for Inhalation, particle diameter (p. 572). The presence of decomposition products was detected by thin-layer chromatography (TLC) using silica gel as the adsorbent layer and ethanol/toluene/acetone/aqueous ammonia/water (25:15:5:4:1) as the developing solvent. For these purposes, samples were taken and stored at 55° C. After one month, they were observed under the microscope and, moreover, subjected to TLC. No spot corresponding to the dispersant or the propellant was noted. The results thus obtained are shown in Tables 3 and 4.

TABLE 4

| Number of times of delivery | Average amount delivered at one time (mg) Example No. | | | | | |
|---|---|---|---|---|---|---|
| | 1 | 2 | 3 | 4 | 5 | 6 |
| 1-10 | 115 | 114 | 111 | 116 | 113 | 110 |
| 11-20 | 114 | 113 | 109 | 115 | 113 | 111 |
| 21-30 | 115 | 113 | 111 | 115 | 112 | 110 |
| 31-40 | 115 | 113 | 110 | 115 | 112 | 110 |
| 41-50 | 115 | 112 | 110 | 115 | 113 | 111 |
| 51-60 | 114 | 113 | 111 | 115 | 113 | 111 |
| 61-70 | 115 | 113 | 111 | 115 | 113 | 110 |
| 71-80 | 114 | 113 | 110 | 114 | 113 | 110 |
| 81-90 | 115 | 112 | 110 | 115 | 112 | 111 |
| 91-100 | 115 | 112 | 110 | 114 | 113 | 110 |

The suspension type aerosol inhalations of the present invention can be prepared by adding 0.015 to 5.00% (w/w) of a finely powdered pyrido[1,2-a]pyrimidine compound and 0.015 to 5.00% (w/w) of a sorbitan fatty acid ester or a decaglycerin fatty acid ester to a propellant. The preparation thus obtained are characterized in that they show little variation in the amount delivered and remain stable during long-term storage. Moreover, the suspension type aerosol inhalations of the present invention can be used for the treatment of both bronchial asthma and allergic rhinitis, simply by replacing the adapter.

The preparation of suspension type aerosol inhalations in accordance with the present invention is illustrated by the following examples. However, these examples are not to be construed to limit the scope of the invention.

EXAMPLE 1

1.0 g of finely powdered AS-35 and 1.0 g of Decaglyn 10-O were placed in an agate mortar and mixed well. 3.6 mg of the resulting mixture was placed in a can and a metered-dose valve was attached thereto. Then, a 4:6 mixture of Freon 11 and Freon 12 was injected through the inlet of the metered dose valve until the contents amounted to 12.0 g. Thereafter, the can was vigorously shaken to obtain a suspension type aerosol inhalation.

EXAMPLE 2

A suspension type aerosol inhalation was prepared in the same manner as in Example 1, except that the mix-

TABLE 3

| Example No. | Pyrido[1,2-a]-pyrimidine compound | | Dispersant | | Propellant [% (w/w)] | Average particle diameter (μm) | | TLC (number of spots) |
|---|---|---|---|---|---|---|---|---|
| | Type | Amount [% (w/w)] | Type | Amount [% (w/w)] | | At the start of the test | At the end of the test | |
| 1 | AS-35 | 0.015 | Decaglyn 10-0 | 0.015 | 99.97 | 3.0 | 3.0 | 1 |
| 2 | | 0.75 | | 0.75 | 98.5 | 3.1 | 3.2 | 1 |
| 3 | | 1.00 | | 5.00 | 94.0 | 3.8 | 3.7 | 1 |
| 4 | | 0.015 | S0-15 | 0.015 | 99.97 | 3.8 | 3.9 | 1 |
| 5 | | 0.75 | | 0.75 | 98.5 | 3.4 | 3.3 | 1 |
| 6 | | 1.00 | | 5.00 | 94.0 | 3.8 | 3.7 | 1 |
| 7 | | 1.00 | | 1.00 | 98.0 | 3.5 | 3.4 | 1 |
| 8 | | 2.00 | | 1.00 | 97.0 | 3.1 | 3.2 | 1 |
| 9 | | 4.00 | | 1.00 | 95.0 | 3.3 | 3.4 | 1 |
| 10 | | 5.00 | | 1.00 | 94.0 | 3.5 | 3.3 | 1 |
| 11 | AS-148 | 0.015 | Decaglyn 7-0 | 0.015 | 99.97 | 3.8 | 3.6 | 1 |
| 12 | | 0.75 | | 0.75 | 98.5 | 3.2 | 3.1 | 1 |
| 13 | | 1.00 | | 5.00 | 94.0 | 3.8 | 3.6 | 1 |
| 14 | | 0.015 | S0-10 | 0.015 | 99.97 | 3.3 | 3.4 | 1 |
| 15 | | 0.75 | | 0.75 | 98.5 | 3.5 | 3.3 | 1 |
| 16 | | 1.00 | | 5.00 | 94.0 | 3.4 | 3.5 | 1 |
| 17 | | 2.00 | S0-15 | 1.00 | 97.0 | 3.3 | 3.3 | 1 |
| 18 | | 5.00 | | 1.00 | 94.0 | 3.2 | 3.4 | 1 | ture of AS-35 and Decaglyn 10-O was used in an amount of 0.18 g.

EXAMPLE 3

0.5 g of finely powdered AS-35 and 2.5 g of Decaglyn 10-O were placed in an agate mortar and mixed well. 0.72 g of the resulting mixture was placed in a can and a metered-dose valve was attached thereto. Then, a 4:6 mixture of Freon 11 and Freon 12 was injected through the inlet of the metered-dose valve until the contents amounted to 12.0 g. Thereafter, the can was vigorously shaken to obtain a suspension type aerosol inhalation.

EXAMPLE 4

A suspension type aerosol inhalation was prepared in the same manner as in Example 1, except that SO-15 was used in place of Decaglyn 10-O.

EXAMPLE 5

A suspension type aerosol inhalation was prepared in the same manner as in Example 4, except that the mixture of AS-35 and SO-15 was used in an amount of 0.18 g.

EXAMPLE 6

A suspension type aerosol inhalation was prepared in the same manner as in Example 3, except that SO-15 was used in place of Decaglyn 10-O.

EXAMPLE 7

0.05 g of finely powdered AS-35 and 0.05 g of SO-15 were placed in a can and a metered-dose valve was attached thereto. Then, a 3:7 mixture of Freon 11 and Freon 12 was injected through the inlet of the metered-dose valve until the contents amounted to 5.0 g. Thereafter, the can was vigorously shaken to obtain a suspension type aerosol inhalation.

EXAMPLE 8

A suspension type aerosol inhalation was prepared in the same manner as in Example 7, except that AS 35 was used in an amount of 0.1 g.

EXAMPLE 9

A suspension type aerosol inhalation was prepared in the same manner as in Example 7, except that AS-35 was used in an amount of 0.2 g.

EXAMPLE 10

A suspension type aerosol inhalation was prepared in the same manner as in Example 7, except that AS-35 was used in an amount of 0.25 g.

EXAMPLE 11

1.0 g of finely powdered AS-148 and 1.0 g of Decaglyn 7-O were placed in an agate mortar and mixed well. 3.6 mg of the resulting mixture was placed in a can and a metered-dose valve was attached thereto. Then, a 4:6 mixture of Freon 11 and Freon 12 was injected through the inlet of the metered-dose valve until the contents amounted to 12.0 g. Thereafter, the can was vigorously shaken to obtain a suspension type aerosol inhalation.

EXAMPLE 12

A suspension type aerosol inhalation was prepared in the same manner as in Example 11, except that the mixture of AS-148 and Decaglyn 7-O was used in an amount of 0.18 g.

EXAMPLE 13

0.5 g of finely powdered AS-148 and 2.5 g of Decaglyn 7-O were placed in an agate mortar and mixed well. 0.72 g of the resulting mixture was placed in a can and a metered-dose valve was attached thereto. Then, a 4:6 mixture of Freon 11 and Freon 12 was injected through the inlet of the metered-dose valve until the contents amounted to 12.0 g. Thereafter, the can was vigorously shaken to obtain a suspension type aerosol inhalation.

EXAMPLE 14

A suspension type aerosol inhalation was prepared in the same manner as in Example 11, except that SO-10 was used in place of Decaglyn 7-O.

EXAMPLE 15

A suspension type aerosol inhalation was prepared in the same manner as in Example 14, except that the mixture of As-148 and SO-10 was used in an amount of 0.18 g.

EXAMPLE 16

A suspension type aerosol inhalation was prepared in the same manner as in Example 13, except that SO-10 was used in place of Decaglyn 7-O.

EXAMPLE 17

A suspension type aerosol inhalation was prepared in the same manner as in Example 7 except that AS-148 was used in an amount of 0.1 g.

EXAMPLE 18

A suspension type aerosol inhalation was prepared in the same manner as in Example 7 except that AS-148 was used in an amount of 0.25 g.

EXAMPLE 19

1.0 g of finely powdered AS-163 and 1.0 g of Decaglyn 10-S were placed in an agate mortar and mixed well. 36 mg of the resulting mixture and 24 mg of finely powdered myristyl-gamma-picolinium chloride were placed in a can and a metered-dose valve was attached thereto. Then, a 4:6 mixture of Freon 11 and Freon 12 was injected through the inlet of the metered-dose valve until the contents amounted to 12.0 g. Thereafter, the can was vigorously shaken to obtain a suspension type aerosol inhalation.

EXAMPLE 20

0.5 g of finely powdered AS-168 and 2.5 g of SO-30 were placed in an agate mortar and mixed well. 0.72 g of the resulting mixture and 24 mg of finely powdered sodium sulfate were placed in a can and a metered-dose valve was attached thereto. Then, a 4:6 mixture of Freon 11 and Freon 12 was injected through the inlet of the metered-dose valve until the contents amounted to 12.0 g. Thereafter, the can was vigorously shaken to obtain a suspension type aerosol inhalation.

EXAMPLE 21

A suspension type aerosol inhalation was prepared in the same manner as in Example 1, except that a 4:6 mixture of Freon 114 and Freon 12 was used in place of the 4:6 mixture of Freon 11 and Freon 12.

EXAMPLE 22

A suspension type aerosol inhalation was prepared in the same manner as in Example 11, except that 4:6 mixture of Freon 114 and Freon 12 was used in place of the 4:6 mixture of Freon 11 and Freon 12.

EXAMPLE 23

A suspension type aerosol inhalation was prepared in the same manner as in Example 19, except that a 4:6 mixture of Freon 114 and Freon 12 was used in place of the 4:6 mixture of Freon 11 and Freon 12.

EXAMPLE 24

A suspension type aerosol inhalation was prepared in the same manner as in Example 20, except that a 2:6:4 mixture of Freon 11, Freon 12 and Freon 114 was used in place of the 4:6 mixture of Freon 11 and Freon 12.

EXAMPLE 25

A suspension type aerosol inhalation was prepared in the same manner as in Example 1, except that a 4:6 mixture of Freon 123 and Freon 124 was used in place of the 4:6 mixture of Freon 11 and Freon 12.

EXAMPLE 26

A suspension type aerosol inhalation was prepared in the same manner as in Example 11, except that a 6:4 mixture of Freon 134a and Freon 141b was used in place of the 4:6 mixture of Freon 11 and Freon 12.

EXAMPLE 27

A suspension type aerosol inhalation was prepared in the same manner as in Example 19, except that a 4:6 mixture of Freon 225ca and Freon 124 was used in place of the 4:6 mixture of Freon 11 and Freon 12.

EXAMPLE 28

A suspension type aerosol inhalation was prepared in the same manner as in Example 20, except that a 2:6:2 mixture of Freon 123, Freon 134a and Freon 225cb was used in place of the 4:6 mixture of Freon 11 and Freon 12.

What is claimed is:

1. A suspension aerosol composition comprising a propellant containing dispersed therein (a) 0.015 to 6.00% (w/w) of a pyrido[1,2-a]pyrimidine compound of the formula wherein R is a n-propyl or allyl group, A is a tetrazolyl or carboxyl group, and n is a whole number of 0 to 2, and (b) 0.015 to 5.00% (w/w) of a fatty acid ester, the fatty acid ester being soluble in the propellant and the pyrido[1,2-a]pyrimidine compound being present in finely powdered form and being insoluble in the propellant and in the fatty acid ester.

2. An aerosol composition as claimed in claim 1 wherein the fatty acid ester is a sorbitan fatty acid ester or a decaglycerin fatty acid ester.

3. An aerosol composition as claimed in claim 2 wherein the sorbitan fatty acid ester is sorbitan sesquioleate, sorbitan mono-oleate, sorbitan trioleate or sorbitan monoisostearate.

4. An aerosol composition as claimed in claim 2 wherein the decaglycerin fatty acid ester is decaglyceryl decaoleate, decaglyceryl decastearate, decaglyceryl heptaoleate, decaglyceryl pentaoleate, decaglyceryl trioleate, decaglyceryl dioleate or decaglyceryl diisostearate.

5. An aerosol composition as claimed in claim 1, 2, 3 or 4 wherein the pyrido[1,2-a]pyrimidine compound is 9[(4-acetyl-3-hydroxy-2-n-propylphenoxy)methyl]-3-(1H-tetrazol-5-yl)-4H-pyrido[1,2-a]pyrimidin-4-one, 9-[(4-acetyl-3-hydroxy-2-n-propylphenoxy)methyl]-3-[2-(1H-tetrazol-5-yl)ethyl]-4H-pyrido[1,2-a]pyrimidin-4-one, 9-[(4-acetyl-3-hydroxy-2-allylphenoxy)methyl]-3-(1H-tetrazol-5-yl)-4H-pyrido[1,2-a]pyrimidin-4-one or 9-[(4-acetyl-3-hydroxy-2-n-propylphenoxymethyl) 4-oxo-pyrido[1,2-a]pyrimidin-3-yl]acetic acid.

6. Composition of claim 1 wherein the propellant is a fluorine-containing lower hydrocarbon.

7. Composition of claim 1 wherein the pyrido[1,2-a]pyrimidine compound is in the form of particles having a diameter in the range of about 0.01 to 10 μm.

8. Composition of claim 7 wherein at least about 50% of the particles have a diameter of about 2 to 5 μm.

9. Composition of claim 1 further including a solidification inhibitor.

10. Composition of claim 1 further including a density modifier.

11. Composition of claim 1 wherein the composition is contained in a container having a delivery valve for dosage delivery of the composition from the container.

* * * * *